United States Patent [19]

Sauer

[11] 4,010,494
[45] Mar. 8, 1977

[54] CANINE EAR IMPLANT AND METHOD FOR SUPPORTING DEFECTIVE AURICULAR CARTILAGE

[75] Inventor: Barry W. Sauer, Central, S.C.
[73] Assignee: Glasrock Products, Inc., Atlanta, Ga.
[22] Filed: Aug. 15, 1975
[21] Appl. No.: 605,006
[52] U.S. Cl. .......................................... 3/1; 3/1.9; 128/92 C; 119/96
[51] Int. Cl.² .......................................... A61F 1/24
[58] Field of Search ........................ 3/1, 1.9–1.913; 128/92 C, 334 R; 119/96

[56] References Cited
UNITED STATES PATENTS 3,879,767  4/1975  Stubstad .................................... 3/1

OTHER PUBLICATIONS

"Investigation of and Use of Dimethyl Siloxanes, Halogenated Carbons and Polyvinyl Alcohol Subcutaneous Prostheses," by J. B. Brown et al., Annals of Surgery, vol. 152, No. 3, pp. 534–547.

"The Role of Porous Polymeric Materials in Prosthetic Attachment," by B. W. Sauer et al., presented at the Clemson University 5th Annual Biomaterial Symposium, (Apr. 14–18, 1973), pp. 1–8.
"Porous Implant Systems for Prosthesis Stabilization," by C. A. Homsy et al., reprint from Clinical Orthopaedics, No. 89, Nov.–Dec., 1972, pp. 220–235.

*Primary Examiner*—Ronald L. Frinks
*Attorney, Agent, or Firm*—Lane, Aitken, Dunner & Ziems

[57] ABSTRACT

Canine ear implant for strengthening the defective auricular cartilage of the canine ear is formed of a sheet of flexible porous polymeric material adapted in size and shape to be positioned adjacent to either side of the auricular cartilage. The polymeric material comprises a network of interconnected pores throughout its volume having an average pore diameter of between 20 μm – 300 μm, the average pore volume being at least 30%.

5 Claims, 1 Drawing Figure

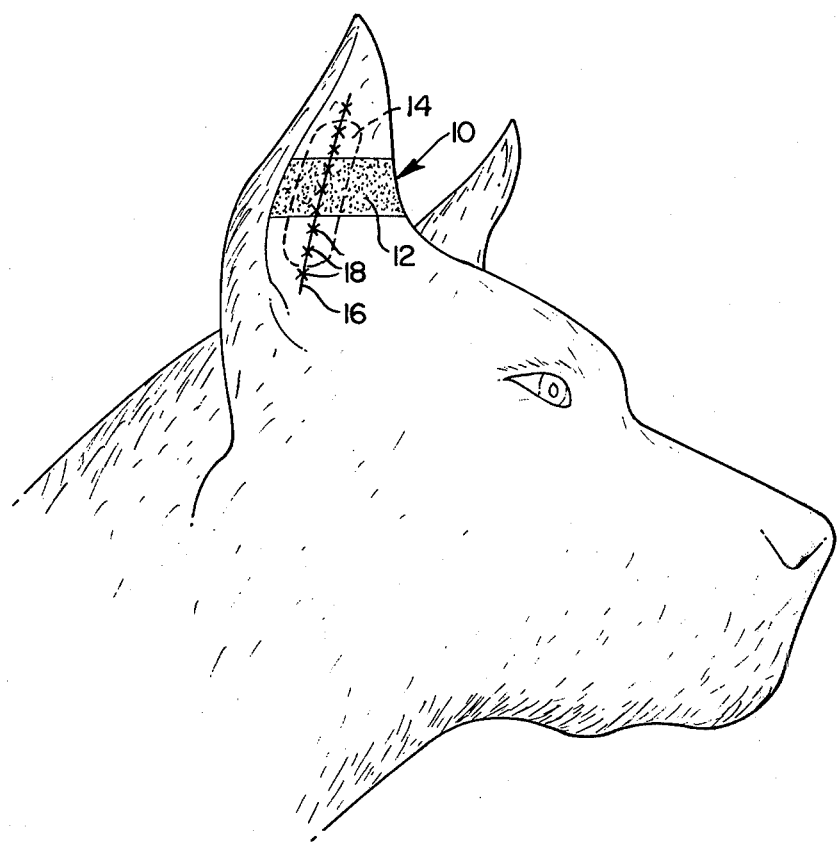

CANINE EAR IMPLANT AND METHOD FOR SUPPORTING DEFECTIVE AURICULAR CARTILAGE

BACKGROUND OF THE INVENTION

This invention relates to prosthetic devices and more particularly to an implant to support weak or defective auricular cartilage in the canine ear.

A collapsed ear is a condition which is common in many dogs and which many people consider unattractive. This condition occurs whenever the auricular cartilage is either weak and cannot support the weight of the ear or whenever the cartilage has been damaged or is otherwise defective and results in the ear remaining in a collapsed position either part or all of the time.

Various types of implanted supports or splints have been used in the past to correct this problem. However, the results have been unacceptable primarily because of the lack of fixation of the implant. This lack of fixation results in a sliding movement of the implant within the ear which causes a gradual wearing away or erosion of adjacent tissue. Eventually, the splint has been found to completely wear away portions of the overlying tissue which allows the splint to extrude from the ear.

Another problem in choosing a material for the use in a canine ear splint is that it be thick enough in order to provide proper support for the ear, but not too thick to result in an unsightly appearance. On the other hand, the material must be thin enough to provide the requisite flexibility.

SUMMARY OF THE INVENTION

In accordance with the invention, it has been found that a thin sheet of a porous polymeric material, such as porous high density polyethylene (HDPE) and porous polypropylene, within certain critical parameters, can be used as a canine ear implant and solve the problems discussed above.

A thin sheet of this material, which will be described in detail below, is surgically implanted over the weakened or defective area in the auricular cartilage, the exact size and shape of the implant depending upon the size and location of the weakened or defective portion of the cartilage and the preference of the veterinarian. The splint may be implanted on either the concave or convex surface of the auricular cartilage, and can be used to support both an axial or transverse defect.

When such a splint is used, it is anchored in place by means of the phenomenon known as tissue ingrowth. This is where tissue will actually grow into and fill the pores of the porous materials. This phenomenon has been recognized as a useful means for anchoring prosthetic devices.

It has been found that porous polymeric materials are particularly suited for use in a prosthetic device such as the canine ear implant because they include an internal network of interconnected pores without sacrificing any of the required strength. Furthermore, the pores are characterized by the fact that in the network there are, for the most part, no straight paths longer than the diameter of the largest pore, a feature which is characterized by the term "tortuousity". This is advantageous because the ingrown tissue will firmly anchor the ear splint in place and prevent any movement of it as the dog flexes his ear. Thus, the erosion problem present in prior art devices is significantly reduced.

In order for the porous polymeric material to include a network of the proper pore size to allow the necessary tissue ingrowth and still retain the strength required to withstand stress to which the ear splint is subjected, it has been found that the material must also have the following characteristics:

1. density — between 0.945 and 0.965 g./cc. for porous HDPE and between 0.912 and 0.914 g./cc. for porous polypropylene, 2. molecular weight number — greater than 450,000 and up to over 6,000,000 depending on the availability of such material, which is the relative mass of a compound calculated in the basis of an atomic weight for oxygen of 16 and is derived by multiplying the atomic weight of each element of the compound by the number of atoms of that element in the compound and adding them all together, 3. melt index — between 0.005 and 5 (ASTM D1238-57T), which includes the combination of materials of different melt indexes within the above range, such as for example a blend of porous HDPE comprising 20% by weight of 0.960 density and 5 melt index and 80% of 0.960 density and 0.01 melt index, 4. average pore diameter — between 20 $\mu$m and 300 $\mu$m, as determined by the bubble technique ASTME 128) or by the Aminco Micro/Macro Porosimeter distributed by the American Instrument Company, and varies according to the tissue, e.g. tendons and/or bone, in which the prosthesis is to be used, 5. average pore volume - minimum of 30% by weight, as determined by comparing the weight of the porous material with the weight of the material if it were not porous, which allows for proper random fixation (ingrowth) of the surrounding tissue without causing the device to fall below the minimum intrinsic strength needed to function properly.

It should also be kept in mind that although the ear implants are preferably formed of porous HDPE or porous polypropylene, any other polymeric material that includes (1) the interconnected network of pores, (2) biocompatibility, and (3) the necessary strength, can be used.

BRIEF DESCRIPTION OF THE DRAWING

For a better understanding of the invention, reference may be had to the following description of an exemplary embodiment taken in conjunction with the accompanying drawing, in which:

FIG. 1 is a front view of the inner portion of a dog ear, showing in particular the position of the inventive ear implant and the incision through which it has been inserted.

DETAILED DESCRIPTION OF AN EXEMPLARY EMBODIMENT

Now, referring to FIG. 1, an exemplary embodiment of the invention will be shown in which the inventive ear splint is used to repair a transverse defect or otherwise weakened portion in the dog ear 10, the shaded portion illustrated by reference numeral 12 representing the weakened portion. In this embodiment the splint 14 has been inserted through the incision 16 and positioned adjacent to the inner or concave surface of the auricular cartilage. As shown, the incision has been closed by the stitches 18. It should be kept in mind, however, that although in FIG. 1 the implant 14 is shown as being generally rectangular in shape with rounded edges and extending almost the full length of the ear, for other defects in other portions of the auricular cartilage implants of different sizes and shaped can be provided.

It has been found that the thickness of the implant will vary, depending on the size of the ear in which it will be used. The implant must be thick enough to contain a porous network sufficient to accommodate enough tissue ingrowth to anchor the implant in place, without eliminating the tortuous character of the pores and without weakening the implant, and still be thin enough to retain the proper flexibility so that the ear can bend. For most dogs the implant should have a thickness of between about 20/1000 to 120/1000 of an inch thick, and slightly larger for extremely large dogs. Moreover, in order to accommodate the tissue ingrowth, it has been found that the average pore diameter should range from 20 μm to about 300 μm.

By providing the ear splint with characteristics that fall within the above parameters, a weakened or defective auricular cartilage can be repaired by an ear implant that will be firmly fixed in place after the tissue ingrowth occurs. This normally takes several weeks. After the tissue ingrowth is completed the ear splint will retain its flexibility and allow the ear to bend, but will not move around within the ear to wear away or erode adjacent tissue.

Accordingly, a novel canine ear splint is provided which solves the problems discussed above and corrects the collapsed ear condition that occurs in many dogs. The embodiment of the invention described above is intended to be merely exemplary to those skilled in the art and they will be able to make modifications and variations thereto without departing from the spirit and scope of the appended claims.

I claim:

1. Canine ear implant for strengthening a defective auricular cartilage of a canine ear, comprising a sheet of flexible polymeric material adapted in size and shape to be positioned adjacent to either side of the auricular cartilage, the polymeric material having a density of at least 0.912 g./c.c. and being porous throughout and comprising a network of interconnected pores with no straight paths longer than the diameter of the largest pore, the minimum pore volume being 30% and the average pore diameter being 20 μm - 300 μm, the sheet having a thickness of at least 20/1000 in.

2. The implant in claim 1, wherein the sheet is generally rectangular in shape with rounded edges.

3. The implant in claim 1, wherein the polymeric material comprises polyethylene having a density in the range of 0.945 and 0.965 g./cc.

4. The implant in claim 1, wherein the polymeric material comprises polypropylene having a density in the range of 0.912 and 0.914 g./cc.

5. Method of strengthening auricular cartilage in a canine ear which has a defective portion, comprising the steps of forming an incision in the outer surface of the ear in the vicinity of the defective portion, implanting a splint adjacent to one side of the defective portion of the cartilage, the splint projecting beyond the defective portion and being formed of a sheet of flexible polymeric material which includes a network of interconnected pores throughout its volume with an average pore diameter of between 20 μm — 300 μm, the sheet having a thickness of at least 20/1000 in.

* * * * *